United States Patent [19]

Vegezzi

[11] 4,190,675

[45] Feb. 26, 1980

[54] METHOD FOR THE PREPARATION OF VERBENONE, MYRTENAL AND PINOCARVEOL AND THEIR THERAPEUTICAL USE

[75] Inventor: Davide Vegezzi, Massagno, Switzerland

[73] Assignee: Enrico Corvi Mora, Piacenza, Italy

[21] Appl. No.: 926,424

[22] Filed: Jul. 20, 1978

Related U.S. Application Data

[62] Division of Ser. No. 801,260, May 27, 1977, abandoned.

[30] Foreign Application Priority Data

Jun. 3, 1976 [CH] Switzerland ............... 7042/76

[51] Int. Cl.$^2$ ............................................. A61K 31/12
[52] U.S. Cl. ................................................... 424/331
[58] Field of Search ........................................ 424/331

[56] References Cited

PUBLICATIONS

Chem. Abst., vol. 71, 102029z, (1969).

*Primary Examiner*—Stanley J. Friedman
*Attorney, Agent, or Firm*—Stevens, Davis, Miller & Mosher

[57] ABSTRACT

Balsamics such as verbenone, myrtenal and pinocarveol can be prepared from an oxidized mixture of terpenes by subjecting such a mixture coming from the oxidation of pinenes to a strong oxidizing treatment followed by the separation of the carbonyl compounds and the vacuum fractional distillation of the resultant mixture so as to recover the expected compounds in a state of very high purity. The balsamic compounds in question are useful in the treatment of bronchopneumonial diseases and each of such compounds has specific indications of its own according to the individual pathological pattern concerned.

1 Claim, No Drawings

METHOD FOR THE PREPARATION OF VERBENONE, MYRTENAL AND PINOCARVEOL AND THEIR THERAPEUTICAL USE

This is a division of application Ser. No. 801,260 filed May 27, 1977, now abandoned.

This invention relates to the preparation of verbenone, myrtenal and pinocarveol starting from oxidized terpene mixtures, and their use in the therapeutics of bronchopneumonial diseases.

The preparation of verbenone and myrtenal starting from alpha-pinene by oxidizing self-catalysis in the presence of salts of chromium, cobalt, and others has been repeatedly described with yield of from 15% to 20%. One of the reasons for the low reaction yields is the formation of side-products of the homolytic reaction (radicalic reaction) such as verbenols and myrtenols, these latter being alcohols which cannot be further oxidized to the ketones in the specific reaction medium.

In the Swiss Patent Specification No. 542 163 of the same applicants hereof, a method is described for the preparation of terpene fractions which are useful in the treatment of bronchopneumonial diseases, said method being based on the oxidation of mixtures which predominantly contain alpha-pinene. More particularly, with the method according to the above mentioned Swiss patent, two terpene fractions are obtained, which distill, respectively, in the temperature ranges of from 40° C. to 60° C. and of from 65° C. to 103° C.

It has now been found, and this is the subject-matter of the present invention, that such oxidation mixtures can be subjected to an additional treatment which, in the case of the preparation of verbenone and myrtenal, is a further oxidation treatment to be carried out with chromium trioxide in sulfuric acid, whereas, in the case of pinocarveol, it consists in opening the oxyrane ring of the alpha-pinene epoxide and subsequent transposition of the resultant compound.

It has been found, in fact, that in the case of verbenone and myrtenal, in the oxidizing treatment with chromium trioxide in sulfuric acid of the oxidation mixtures of the Swiss patent afore-mentioned, the oxidative method goes on with a total disappearance of the alcohols and a formation of carbonyl compounds (ketones and aldehydes). Upon treatment with chromium trioxide in sulfuric acid an isolation of the as-obtained ketone bodies is accomplished by a bisulfite complex and fractional distillation.

In the case of pinocarveol the opening of the oxyrane ring is preferably carried out with aluminum isopropoxide, whereafter the removal of the carbonyl compounds and the fractional distillation are proceeded with in order to isolate pinocarveol.

As regards the therapeutical use of the compounds obtained with the method according to the present invention, the therapeutical use of the terpene fractions disclosed in the Swiss Pat. No. 542,163 is already known, and more particularly the use of the fraction which distills in the 65° C.–103° C. range (to be indicated hereinafter as the "fraction 2").

The balsamic and analeptic actions of such fraction 2 are already known, the therapeutical use of such fraction being just due to such actions.

In addition to the uncertainty from a scientific standpoint as to the exact identification of the active principles which are responsible for the therepeutical activity of pharmaceutical compositions based on such fraction 2, the drawback is apparent, from an industrial viewpoint, of working on a mixture of compounds having a composition which is changeable, even within a certain range. In addition, the fact is worth noting that the pharmaceutical composition containing the fraction 2 has a general indication as a balsamic, along with a few side activities, without any possibility being afforded of exalting the one of these activities preferably over the others, or of improving the general activity.

It has now been found, and this is another aspects of the present invention, that the terpene compounds in question possess, in addition to a some already known actions, such as the balsamic and the analeptic actions, also appreciable bronchodilating, anti-phlogistic, antiexudative and antiaggregative actions.

The demonstration of the pharmacological activity of verbenone, pinocarveol and myrtenal is based on the following parameters:
1. Acute toxicity
2. Action on the bronchial muscles
3. Action on the inflammatory process
4. Action on haemolysis
5. Action on the thrombocyte aggregation
6. Antibacterial action.

In all these tests, the activity of the different compounds has been compared, with that of the fraction 2 as defined above and with that of therapeutical preparations based on terpene alcohols, more particularly sobrerol.

The individual compounds the subject of the present invention will be now considered:

A. Verbenone

1. Acute Toxicity

TABLE 1 reports the $ID_{50}$ (and the fiducial limits 95%) as determined according to the Litchfield and Wilcoxon method (J. Pharmacol. Exp. Ther., 96, 99, 1949), by administering verbenone both intraperitoneally (i.p.) and orally (p.o.) to groups of 10 mice and 6 rabbits per dose.

TABLE 1

| COMPOUND | Animals | Sex | Administration route | $LD_{50}$ milligrams per kg/b.w. | Gleason classification |
|---|---|---|---|---|---|
| | Mice | male | i.p. | 361 (337–385) | Poor |
| | | female | | 325 (308–343) | |
| VERBENONE | Mice | male | p.o. | 1410 (1165–1706) | Slight |
| | | female | | 1530 (1124–1912) | |
| | Rabbits | male | i.p. | 310 (250–384) | Poor |
| | | female | | 232 (197–274) | |
| | Rabbits | male | p.o. | 790 (608–1027) | Poor |
| | | female | | 655 (570–753) | |

On the basis of these data the verbenone appears a well tolerated compound, since its toxicity is of the slight or poor magnitude according to the Gleason classification, as related to the animal species and the administration route.

2. Bronchodilating activity

The verbenone has exhibited, both in vitro and in vivo a pronounced bronchodilating activity, by virtue of which it distinguishes in a statistically significant way both over the other medicinal substances present in the fraction 2 of the Swiss Pat. No. 542,163 and over the reference terpene, i.s. sobrerol.

a—in vitro

On the Guinea-pig trachea, isolated according to the technique by Costantine (J. Pharm. Pharmacol., 17, 384, 1965), the verbenone brings about the relaxation of the smooth tracheal muscles at the concentration of 125 to 2,000 micrograms per milliliter with an intensity which is significantly higher than that of the terpenes of the fraction 2 and also than that of sobrerol (TABLE 2). In addition, at concentrations in the range of from $10^{-3}$ M to $5.10^{-3}$ M, it inhibits the histamine-induced contractions of the isolated Guinea-pig trachea (Histamine $10^{-5}$ M, see TABLE 3).

TABLE 2

Percentages of relaxation (average ± standard deviation of 4 preparations) of the isolated Guinea-pig trachea as brought about by concentrations of 125–500 and 2,000 micrograms per milliliter.

| COMPOUND | Preparations N° | | 125 μg/ml | 500 μg/ml | 2,000 μg/ml |
| --- | --- | --- | --- | --- | --- |
| VERBENONE | | ave. | 26.25 | 61.25 | 71.37 |
| | 4 | | | | |
| | | std.dev. | 2.39 | 2.39 | 1.15 |
| FRACTION 2 | | ave. | 13.5 | 33.75 | 52.25 |
| | 4 | | | | |
| | | std.dev. | 1.70 | 1.49 | 2.95 |
| SOBREROL | | ave. | 1.87 | 5.62 | 20.75 |
| | 4 | | | | |
| | | std.dev. | 1.19 | 2.13 | 1.49 |

TABLE 3

Verbenone percentages of inhibition of the histaminic spasm due to relaxation of the smooth tracheal muscles (average ± standard deviation of preparations).

| CONCENTRATION | $10^{-3}$M | $5.10^{-3}$M |
| --- | --- | --- |
| Average | 29.2 | 96.8 |
| Standard deviation | 5.1 | 16.6 | b. in vivo

The verbenone injected intravenously in anesthesized dogs at dosages of from 0.6 milligrams per kilogram body weight to 4.8 mgs/kg/b.w. produces a pronounced reduction of the lung resistances as determined according to the technique by Diamond (Arch. Int. Pharmacodyn., 168, 239, 1967) (see TABLE 4). In addition, verbenone perfused intravenously in rabbits at the dose unit of 2.5 mls per kilogram b.w. per minute, inhibits the histamine-induced experimental bronchospam (histamine 100 micrograms per kilogram b.w. intravenously) to a degree which is statistically higher than that of the terpenes of the fraction 2 and also than that of sobrerol (TABLE 5).

TABLE 4

| VERBENONE - | Percentage reductions of the Lung Resistance by intravenous administration to dogs (Average ± Standard deviation for 4 animals).- | | | |
| --- | --- | --- | --- | --- |
| Dosage mgs/kg b.w. | 0.6 | 1.2 | 2.4 | 4.8 |
| Average | 7.175 | 10.85 | 22.225 | 30.6 |
| Standard deviation | 6.786 | 7.7 | 18.636 | 13.507 |

TABLE 5

Percentages of inhibition of the histamine-induced bronchospasm by intravenous perfusion in rabbits (average of 4 animals ± standard deviation).

| Perfusion times COMPOUND | | 15 minutes | 30 minutes | 60 minutes |
| --- | --- | --- | --- | --- |
| VERBENONE | average | 36.25 | 46.27 | 73.32 |
| | std.dev. | 1.65 | 9.00 | 7.17 |
| FRACTION 2 | average | 16.30 | 24.20 | 38.92 |
| | std.dev. | 3.62 | 4.39 | 3.67 |
| SOBREROL | average | 2.15 | 1.15 | 3.97 |
| | std.dev. | 4.30 | 6.39 | 8.73 |

3. Anti-inflammatory activity

In albine rats of the COBS (Charles River) stock, verbenone as administered intraperitoneally at the dosage of 30 milligrams per kilogram b.w., inhibits the experimental oedema in the paw as induced by carrageenin (Winter, C.A. et al., Proc. Soc. Exp. Biol. Med., 111, 544, 1962) both in normal rats and in suprarenalectomized rats to a degree which is, from the statistical standpoint, significantly improved over those of the fraction 2 and of sobrerol (TABLE 6).

When administered intraperitoneally in rats at the dosages of 36 and 120 milligrams per kilogram b.w., verbenone displays an intense antiexudative activity in the experimental, turpentine-induced pleuritis (Hurley, J. V. et al., J. Path., 91, 575,1966) to a degree which can be compared to that of aspirin (TABLE 7).

TABLE 6

Anti-inflammatory activity on the carrageenin-induced oedema in rats.-

| COMPOUND | Dosage milligrams/kg b.w. intraperitoneally | % inhibition of plantar oedema, as after 4 hrs. from administration (ave.± Std.dev.on 6 animals |
| --- | --- | --- |
| VERBENONE | 30 | 29 |
| FRACTION 2 | 30 | 21 |

TABLE 6-continued

Anti-inflammatory activity on the carrageenin-induced oedema in rats.-

| COMPOUND | Dosage milligrams/kg b.w. intraperitoneally | % inhibition of plantar oedema, as after 4 hrs. from administration (ave.± Std.dev.on 6 animals) |
|---|---|---|
| SOBREROL | 30 | 11 |

4. Haemolytic activity, in vitro

Verbenone protects in vitro the red blood cells of rats from the haemolysis as induced by capillary-active-agents (Tween 80) with an effective concentration 50% (EC 50) of 639.5 micrograms per kg b.w. (fiducial limits 95% : 518.0–760.11).

5. Antiaggregative activity, in vitro

Verbenone, at concentrations of from 160 to 1.280 micrograms/milliliter inhibits the thrombocyte aggregation from ADP in vitro, evaluated according to the method by Born and Cross (J. Physiol., London, 168, 178, 1963) to a degree which is higher than that of the terpenes of the Fraction 2 and of sobrerol (TABLE 8).

TABLE 7

Activity of Verbenone on the Turpentine-Induced Pleuritis in Rats.-

| Intraperitoneal administration | Exudate, mls. | ± Std.Dev. | Inhibition % | Significativity P |
|---|---|---|---|---|
| Controls (solvent) | 1.97 | 0.24 | — | — |
| Aspirin (100 mgs/kg) | 1.30 | 0.13 | 34 % | <0.01 |
| Verbenone (36 mgs/kg) | 1.23 | 0.24 | 37.6% | <0.01 |
| Verbenone (120 mgs/kg) | 0.97 | 0.22 | 50.1% | <0.01 |

TABLE 8

Thrombocyte aggregation inhibition percentage (average of repeated tests).-

| | FINAL CONCENTRATIONS | | % INHIBITION |
|---|---|---|---|
| CONTROL | | | 0 |
| VERBENONE | 1280 | μg/ml | 100 |
| " | 640 | " | 44 |
| " | 320 | " | 6 |
| " | 160 | " | 0 |
| CONTROL | | | 0 |
| SOBREROL | 4000 | " | 32 |
| " | 2000 | " | 24 |
| " | 1500 | " | 12 |
| " | 1000 | " | 4 |
| CONTROL | | | 0 |
| FRACTION 2 | 1280 | " | 70 |
| " | 1016 | " | 18 |
| " | 806 | " | 14 |
| " | 640 | " | 0 |

6. Antibacterial activity

Verbenone possesses a poor antibacterial activity on the Gram-positive and Gram-negative germs, with a MIC (Minimum Inhibiting Concentration) of 800 micrograms/ml on *Staphylococcus aureus* and *Escherichia coli* (TABLE 9) and is as active as Fraction 2 and more active than sobrerol.

TABLE 9

Minimum Inhibiting Concentrations (MIC) in micrograms per milliliter.-

| Microorganism Compound | Staphylococcus aureus | Escherichia coli |
|---|---|---|
| VERBENONE | 800 | 800 |
| FRACTION 2 | 800 | 800 |
| SOBREROL | ∞ | ∞ |

Summing up, the compound has proven to possess a pronounced bronchodilating action, by virtue of which it distinguishes in a statistically significant manner both over the other medicaments present in Fraction 2 of Swiss Pat. No. 542,163 and the reference terpene (sobrerol).

On account of these particular properties, verbenone is effective as the active ingredient of a pharmaceutical preparation which is especially adapted for the treatment of bronchopneumonial diseases which are accompanied by an obstruction of the respiratory channels due to inflammation and infections causative agents. The dosage envisaged for therapeutical applications is from 10 to 100 milligrams daily.

B—MYRIENAL

1. Acute toxicity

The $LD_{50}$ as determined according to the method by Litchfield and Wilcoxon (J. Pharmacol. Exp. Ther., 96, 99, 1949) by administering the myrtenal intravenously to groups of 10 mice was 170 milligrams per kilogram b.w.

2. Bronchodilatory activity

Myrtenal has shown, both in vitro and in vivo a fair bronchodilating activity.

a—in vitro

On the isolated Guinea-pig trachea according to the technique by Costantine (J. Parm. Pharmacol., 17, 384, 1965), myrtenal determines the relaxation of the tracheal smooth muscles at the concentration of 125–200 micrograms/ml with an intensity which is statistically higher than that of the Fraction 2 and that of sobrerol (TABLE 10).

TABLE 10

Percentage of relaxation (average ± standard deviation of 4 preparations) of the isolated Guinea-pig trachea as determined by concentrations of 125–500 and 2,000 micrograms/milliliter.

| Compound | Preparations N° | | 125 micogr/ml | 500 microgr/ml | 2,000 microgr/ml |
|---|---|---|---|---|---|
| MYRTENAL | 4 | ave. | 7.5 | 47.5 | 62.5 |
| | | std. dev. | 5.0 | 15.0 | 20.7 |
| FRACTION 2 | 4 | ave. | 13.5 | 33.75 | 52.25 |
| | | std. dev. | 1.70 | 1.49 | 2.95 |
| SOBREROL | 4 | ave. | 1.87 | 5.62 | 20.75 |
| | | std. dev. | 1.19 | 2.13 | 1.49 | b—in vivo

Myrtenal perfused intravenously in rabbits at the dosage of 2.5 milliliters per kg b.w. per minute inhibits the experimental histamine-induced bronchospasm (histamine 100 micrograms/kg b.w. intravenously) in a manner which is statistically higher than that of sobrerol and slightly lower than that of Fraction 2 (TABLE 11).

TABLE 11

Percentages of inhibition of the histamine-induced bronchospasm by intravenous perfusion in rabbits (average on 4 animals ± standard deviation).

| Compound | Perfusion times | 15 min. | 30 mins. | 60 mins. |
|---|---|---|---|---|
| MYRTENAL | ave. | 25.4 | 20.4 | 28.8 |
|  | std.dev. | 10.4 | 16.2 | 13.5 |
| FRACTION 2 | ave. | 16.30 | 24.20 | 38.92 |
|  | std.dev. | 3.62 | 4.39 | 3.67 |
| SOBREROL | ave. | 2.15 | 1.15 | 3.97 |
|  | std.dev. | 4.30 | 6.39 | 8.73 |

3. Anti-inflammatory activity

In albino rats of the COBS (Charles River) stock, myrtenal as administered intraperitoneally at the dosage of 30 milligrams per kg b.w. inhibits the experimental paw oedema from injection of carrageenin (Winter, A. C. et al., Proc. Soc. Exp. Biol. Med. 111, 544, 1962) to a degree which is more intense than that of Fraction 2 and also than that of sobrerol (TABLE 12).

TABLE 12

Anti-inflammatory activity on the carrageenin oedema in rats.

| Compound | Dosage mg/kg b.w. intraperitoneally | % inhibition on the plantar oedema after 4 hours as from administration (average on 6 animals ± std. deviation) |
|---|---|---|
| MYRTENAL | 30 | 30 |
| FRACTION 2 | 30 | 21 |
| SOBREROL | 30 | 11 |

4. Antihaemolytic activity, in vitro

Myrtenal et concentrations of from 80 to 500 micrograms/ml protects the red blood cells of rats from the haemolysis as induced by capillary-active agents (Tween 80) with an Effective Concentration 50% equal to 157.09 micrograms/ml (fiducial limits 95% = 112.3–189.9).

5. Antiaggregative activity

Myrtenal at concentrations from 160 to 1,280 micrograms/ml inhibits in vitro the thrombocyte aggregation from ADP, evaluated according to the method by Born and Cross (J. Physiol., London, 168, 178, 1963), to a degree which is higher than those of Fraction 2 and sobrerol.

TABLE 13

Thrombocyte aggregation : % inhibition (average of repeated tests)

| FINAL CONCENTRATIONS | | | % INHIBITION |
|---|---|---|---|
| CONTROL | | | 0 |
| MYRTENAL | 1280 | µg/ml | 75 |
| " | 640 | " | 20 |
| " | 320 | " | 12 |
| " | 160 | " | 0 |
| CONTROL | | | 0 |
| SOBREROL | 4000 | " | 32 |
| " | 2000 | " | 24 |
| " | 1500 | " | 12 |
| " | 1000 | " | 4 |
| CONTROL | | | 0 |
| FRACTION 2 | 1280 | " | 70 |
| " | 1016 | " | 18 |
| " | 806 | " | 14 |
| " | 640 | " | 0 |

6. Antibacterial activity

Myrtenal possesses a pronounced antibacterial activity on Gram-positive germs, less intense on Gram-negative ones with a Minimum Inhibiting Concentration (MIC) of 200 micrograms/ml on *Staphylococcus aureus*, and of 800 micrograms/ml on *Escherichia coli* and is more active both than Fraction 2 and sobrerol. (TABLE 14).

TABLE 14

Minimum Inhibiting Concentrations (MIC) in micrograms/milliliter.

| Microorganism Compound | *Staphylococcus aureus* | *Escherichia coli* |
|---|---|---|
| Myrtenal | 200 | 800 |
| Fraction 2 | 800 | 800 |
| Sobrerol | ∞ | ∞ |

This compound, myrtenal, has shown, by way of conclusion, that it possesses a marked antibacterial action by virtue of which it distinguishes in a statistically significant way from both the terpene mixtures of Fraction 2 of Swiss patent and the other medicinal substances of reference, Myrtenal has an anti-inflammatory action of poor magnitude, it displays an antihaemolytic activity and, finally, it has also a bronchodilating type action and an anti-aggregative action as well.

On account of these particular features thereof, myrtenal is indicated as an active ingredient of medicinal compositions which are particularly suitable for the therapy of bronchopneumonial diseases when an important bacterial component is present, or when, at any rate, an antibiotic-based therapy is required. In connection with such indications, the administration of a daily dosage of from 10 to 100 milligrams of myrtenal is suggested.

C—PINOCARVEOL

1. Acute toxicity

The $LD_{50}$ as determined according to the method by Litchfield and Wilcoxon (J. Pharm. Exp. Ther. 96, 98, 1949) by administering pinocarveol intravenously to groups of 10 rats per dosage was equal to 140 milligrams per kilogram.

2. Bronchodilating activity

Pinocarveol has exhibited, both in vitro and in vivo, a fair bronchodilating action.

a—in vitro

On the Guinea-pig trachea isolated according to the technique by Costantine (J. Pharm. Pharmacol., 17, 384, 1965), pinocarveol determines the relaxation of the smooth tracheal muscles at the concentration of 125–2.000 micrograms/ml with an intensity which is statistically higher than that of sobrerol and which can be compared to that of Fraction 2.

b—in vivo

Pinocarveol perfused intravenously in rabbits at the dosage of 2.5 milligrams per kilogram and per minute inhibits the experimental bronchospasm induced by histamine (100 micrograms per kilogram, intravenously) in a manner which is statistically higher than those of FRACTION 2 and of sobrerol.

3. Anti-inflammatory activity

In albino rats of the COBS (Charles River) stock, pinocarveol administered intravenously at the dosage of 30 milligrams per kg inhibits the experimental paw oedema from injection of carrageenin (Winter, C. A. et al., Proc. Soc. Exp. Biol. Med., 111, 544, 1962) to a degree which is more intense than those of Fraction 2 and of sobrerol.

4. Anti-haemolytic activity, in vitro

Pinocarveol at concentrations of from 20 to 200 micrograms/ml protects the red blood cells of rats from the haemolysis caused by capillary-active agents (Tween 80) with an Effective Concentration 50% (EC 50) of 132.29 micrograms/ml (Fiducial limits 95%=111.5-153.04).

5. Anti-aggregative activity

Pinocarveol at concentrations of from 160 to 1.280 micrograms/ml inhibits, in vitro, the thrombocyte aggregation due to ADP, evaluated according to the method by Born and Cross (J. Physiol., London, 168, 178, 1963) to a degree which exceeds that of the terpenes of the Fraction 2 and that of sobrerol.

6. Anti-bacterial activity

Pinocarveol is endowed with a poor antibacterial activity both on Gram-positive and Gram-negative germs with a MIC (Minimum Inhibiting Concentration) of 800 micrograms/ml on *Staphylococcus aureus* and *Escherichia coli* and is thus more active than sobrerol and as active as Fraction 2.

Summing up, the compound pinocarveol has proven to possess a pronounced anti-inflammatory action by virtue of which it distinguishes in a statistically significant manner from the other medicinal substances such as the mixture of Fraction 2 of the Swiss Patent aforementioned and the reference terpene (sobrerol).

Pinocarveol possesses a poor bronchodilating action and is also endowed with a pronounced antihaemolytic activity, by virtue of which it is possible to attribute to such compound a stabilizing action at the cellular membrane level.

Pinocarveol displays a poor antibacterial action and also exhibits a conspicuous antiaggregative action.

On account of its particular properties, pinocarveol can be the active ingredient of a medicament which is particularly suitable for the treatment of bronchopneumonial diseases which are accompanied by a strong inflammatory pattern of the respiratory channels.

The dosages to be recommended for this therapeutic application are from 10 to 100 milligrams daily.

The pharmaceutical compositions according to the present invention can be presented in the form of preparations for oral administration, normal or delayed-action, such as soft capsules, or injectable ampoules, suppositories, sprays in various solution forms, ointments and balms with the usual media, fillers and so on as conventionally used in the pharmaceutical art, both as individual components and in association with medicaments indicated in the diseases referred to above, that is, antibiotics, antibacterial substances, chemotherapeutic substances, sulfonamide drugs, anti-inflammatory drugs, cortisone preparations and analgesics.

The following examples are intended to illustrate without limitation the preparation of the compounds according to the present invention.

EXAMPLE 1 a—Alcohol oxidation 100 grams of the terpene mixture of Fraction 2 of the Swiss Pat. No. 542 163, 20-30% of which comprises compounds having a carbonyl moiety (predominantly verbenone and myrtenal) whereas 50-60% comprises compounds having an alcoholic moiety (mainly verbenol and myrtenol) are dissolved in 2,000 mls of dry acetone.

Separately, the oxidizing solution is prepared by admixing cautiously 37.41 grams of $CrO_3$ with 32.2 mls of conc. $H_2SO_4$ in the quantity of water which is sufficient to make up a final volume exactly equal to 140 mls.

The chromic acid is then added slowly and dropwise to the acetone solution with stirring, cooling on an ice bath so as to maintain the temperature constantly below 30° C. On completion of the addition, filtration is carried out on a Celite (Trade Mark) and the filtrate is taken up by evaporating off acetone under reduced pressure at 40° C. The residue is then diluted with water, neutralized in cold conditions with 10% NaOH and extracted with $CHCl_3$ until exhausting the mother liquors. The combined organic extracts are dried over anhydrous $Na_2SO_4$ and evaporated to dryness under reduced pressure at 40° C.

By so doing, there are obtained about 100 grams of a raw product which is composed, for 50-60% by compounds having a carbonyl moiety (prevailingly verbenone and myrtenal).

b—Separation of the carbonyl compounds from the raw material as obtained from the oxidation run An appropriate vessel is charged with 100 grams of a raw mixture as obtained from the stage a of this method, dissolved in 500 mls of ether and a solution formed by 120 grams of $NaHSO_3$ and 72 grams of $NaHCO_3$ in 2,000 mls of water. The mixture is vigorously shaken during about 20 hours at room temperature, and then transferred to a separatory funnel and the organic phase is discarded. The aqueous phase is washed twice with 500 mls of ether each time, whereafter the aqueous bisulfite solution is taken up and subjected to steam distillation. The processing of the distillate gives 50-55 grams of a mixture which is virtually composed by pure verbenone and myrtenal.

c—Obtention of pure verbenone and myrtenal 50 grams of the product coming from the previous stage are subjected to fractionation in a vacuo at 20 millimeters of mercury, using a reflux column filled with nickel shavings. The distillation is carried out slowly (5 to 8 mls/hour) by maintaining a reflux ratio of about 40 to 1 the whole run throughout. The fraction which distills at 90° C.-95° C. is composed by myrtenal (19 grams) and has the following physico-chemical specifications:

$n_D^{20}=1.50$; $d_{20}=0.98$.

Infrared Analysis: bands at 1684 cm$^{-1}$ $\gamma$ C=O (conjugated); 1623 cm$^{-1}$ $\gamma$ C=C (conjugated); 1471 cm$^{-1}$ $\gamma$ C—H; 1423-1387-1372.

UltraViolet Analysis $\lambda_{max}$ (EtOH)=246 nm ($\epsilon$ about 8400).

The semicarbazone melts at 210° C.-215° C.

The fraction which distills subsequently at 110° C.-113° C. at 20 millimeters of mercury is composed by verbenone (28.5 grams) and has the following physico-chemical specifications:

$n_D^{20}=1.49$; $d_{20}=0.97$.

Infrared bands at 1670 cm$^{-1}$ $\gamma$ C=O (conjugated); 1615 cm$^{-1}$ $\gamma$ C=C (conjugated); 1650-1435-1370.

Ultraviolet $\lambda_{max}$(EtOH)=250 nm $\epsilon$=7,300.

Semicarbazone: m. point 188° C.-190° C.

EXAMPLE 2 a—Conversion of alpha-pinene epoxide into pinocarveol 60 grams of the terpene mixture of Fraction 2 of the Swiss Pat. No. 542 163.10-15% of which comprises alpha-pinene epoxide, whereas 20-30% consists of compounds having a carbonyl moiety, and 50-60% consists of compounds having an alcoholic moiety (verbenol, pinocarveol and myrtenol), are dissolved in 60 mls of anhydrous toluene. To the solution is added an excess of aluminum isopropoxide (about 2-3 grams) and the mixture is boiled during 10 minutes. The mixture is carefully cooled and slowly acidified by cautiously adding diluted sulfuric acid, while still keeping at a temperature of 0° C. or below. The phases are separated, the liquors are exhausted with toluene, the organic solutions combined, washed with water and dried over anhydrous Na$_2$SO$_4$. Filtration is carried out and evaporation at 60° C. under reduced pressure is effected until a solid residue is obtained. There are obtained about 60 grams of a raw product which is exempt from epoxide and is enriched with compounds having an alcoholic function (pinocarveol, verbenol and myrtenol).

b—Separation of the carbonyl compounds

The residue which has been obtained from the previous stage is taken up with 300 mls of diethyl ether and the resultant solution is subjected to vigorous stirring with a mixture formed by 60 grams of NaHSO$_3$, 36 grams of NaHCO$_3$ and 1,000 mls of water, such treatment being carried out during 20 hours at room temperature. The mixture is transferred into a separatory funnel and the phases are separated. The aqueous phase contains myrtenal and verbenone in the form of soluble bisulfite adducts, from which they can be recovered in the form of pure products by working according to what has been indicated for the previous stages. The organic phase, which contains the alcoholic compounds, is washed to neutrality with water, dried over Na$_2$SO$_4$, filtered and evaporated to dryness under reduced pressure. There are obtained 40-50 grams of a residue which is predominantly composed by pinocarveol, verbenol and myrtenol.

c—Obtention of pure pinocarveol

The residue coming from the previous stage is subjected to a series of fractional distillation under vacuum, at 20 millimeters of mercury, using a reflux column filled with nickel shavings. The distillation is carried out slowly (5-6 mls/hour) by maintaining a reflux ratio of about 40:1 during the entire run. The fraction which distills at 100° C.-106° C. under 20 millimeters of mercury and which is strongly enriched with pinocarveol, is collected and subjected to redistillation under the same conditions. There are obtained 15-18 grams approx. of 95%-98% pure pinocarveol which has the following physico-chemical specifications: b.point: 103°-104° C. under 20 mm Hg $n_D^{20}=1.4988$; $d_4^{20}=0.98$.

Infrared analysis: characteristic bands of terminal double bond at 6.00 microns and at 11.20 microns.

I claim:

1. The process of treating inflammation of the bronchia comprising administering from 10 to 100 milligrams/day of verbenone to a patient having inflammation of the bronchia.

* * * * *